Figure 1:
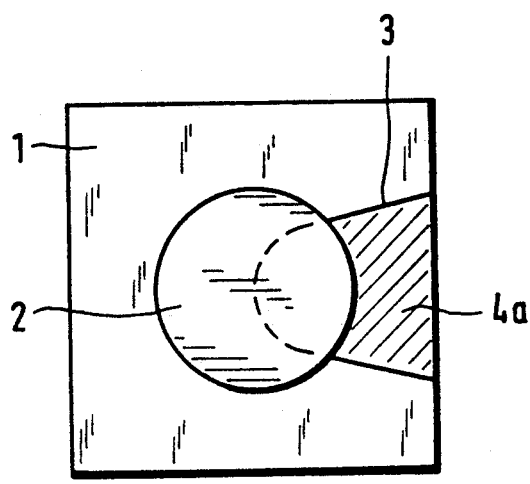

United States Patent [19]

Hoffmann et al.

[11] Patent Number: 5,242,381
[45] Date of Patent: Sep. 7, 1993

[54] APPLICATION AID AND THE USE THEREOF

[75] Inventors: Hans-Rainer Hoffmann; Walter Müller, both of Neuwied; Heinrich Kindel, Rengsdorf, all of Fed. Rep. of Germany

[73] Assignee: LTS Lohmann Therapie- Systeme GmbH & Co. KG., Neuwied, Fed. Rep. of Germany

[21] Appl. No.: 827,550

[22] Filed: Jan. 29, 1992

Related U.S. Application Data

[63] Continuation of Ser. No. 576,623, Aug. 31, 1990, abandoned.

[30] Foreign Application Priority Data

Sep. 16, 1989 [DE] Fed. Rep. of Germany ....... 3931019

[51] Int. Cl.⁵ .................... A61F 13/00; A61F 15/00; A61B 17/06; A61B 19/02
[52] U.S. Cl. ........................................ 602/57; 602/58; 602/59; 206/440; 206/815
[58] Field of Search ............... 206/484, 440, 813, 804, 206/815; 602/57, 58, 59

[56] References Cited

U.S. PATENT DOCUMENTS

| | | | |
|---|---|---|---|
| 1,862,122 | 6/1932 | Schrader | 128/156 |
| 1,926,553 | 9/1933 | Morse | 206/813 |
| 2,037,343 | 4/1936 | Scholl | 206/440 X |
| 2,052,072 | 8/1936 | Baumwell | 128/156 |
| 2,491,281 | 12/1949 | Rowe | 206/813 |
| 2,563,689 | 8/1951 | Muhlhauser | 206/440 X |
| 2,685,086 | 8/1954 | Henry | 128/155 |
| 3,162,306 | 12/1964 | Zackheim | 206/440 |
| 3,301,392 | 1/1967 | Regan, Jr. | 206/484 |
| 3,370,365 | 2/1968 | Vosbikian | 206/484 |
| 3,556,096 | 1/1971 | Fuller et al. | 128/171 |
| 3,809,220 | 5/1974 | Arcudi | 206/484 |
| 4,394,904 | 7/1983 | Larimore | 206/813 |
| 4,627,429 | 12/1986 | Tsuk | 128/156 |
| 4,666,040 | 5/1987 | Murata | 206/440 X |
| 4,807,613 | 2/1989 | Koehnke et al. | 128/155 |
| 4,815,457 | 3/1989 | Mazars et al. | 128/155 |
| 4,928,680 | 5/1990 | Sandbank | 128/155 |
| 4,966,138 | 10/1990 | Chow et al. | 128/155 |

Primary Examiner—Randall L. Green
Assistant Examiner—Elizabeth M. Burke
Attorney, Agent, or Firm—Sprung Horn Kramer & Woods

[57] ABSTRACT

An application aid for one or several articles, such as therapeutic systems, plasters, labels, or the like, adhering to and positioned in a mechanically releasable manner on a carrier or covering layer, respectively, which extends in sheet-like form and particularly is flexible, in the form of cuts or predetermined breaking lines formed within the carrier or covering layer is characterized in that each article (2) is assigned a portion (4, 4a) of the carrier or cover layer (1), which portion laterally projects said article and is removable from the rest of the carrier or cover layer (1) by means of non-linear cuts or predetermined breaking lines, whereby the cuts or predetermined breaking lines connect two points at the edge of the carrier or cover layer and at least partially run below the contact surface of the articles, at least one of these points lies on that portion of the carrier or covering layer projecting the articles at the side, and the imaginary straight connecting line between these two points, except for the starting and the final point, does not exhibit any other points of intersection with the cuts or predetermined breaking lines.

7 Claims, 2 Drawing Sheets

APPLICATION AID AND THE USE THEREOF

This application is a continuation, of application Ser. No. 576,623, filed Aug. 31, 1990, now abandoned.

Application aid for articles adhering in a mechanically removable manner to a carrier or covering layer, respectively, extending in a sheet-like form.

The present invention relates to an application aid for one or more articles, such as therapeutic systems, plasters, labels, or the like, positioned on a planiform extending, particularly flexible carrier or covering layer in an adhesive but mechanically releasable manner in the form of cuts or predetermined breaking lines formed in the carrier or cover layer, respectively.

Many ways of arranging articles adhesively on a base material and to remove them if required are known. This, for example, can have the purpose of keeping the articles available in an easily accessible way. However, this possibility is particularly made use of, if specially prepared surfaces of articles are to be protected against any influence until they are applied. For example, it is known to cover and protect the pressure-sensitive adhesive layer of labels, as well as plasters and other articles, by means of a removable protective foil until they are applied or used.

Removing the articles from a carrier layer or pulling-off the cover layer, respectively, to expose the area to be protected is particularly difficult, if an adhesive composite between two materials is concerned. This particularly applies to those cases where the article surface to be protected is to be saved from damage and/or contamination both during and after exposure by removing the carrier or cover layer, e.g., in order to maintain the adhesiveness of an adhesive layer, the intactness of sensitive surfaces against mechanical influences, a seal of the surface, e.g., against escape of volatile components applied to the surface, and so on.

Particularly if one tries to separate the partners by means of the fingernails, a knife, or any other instrument, undesired contact or even damage of the surface to be protected occur. In addition, it may happen that there is no complete separation of the partners, i.e., portions of the carrier or cover layer remain sticking to the surfaces to be protected, which then are very difficult to remove from the surface without damaging it.

Such a procedure cannot be applied particularly if the area to be protected is a sterile surface of a bandage, the skin contact layer of a therapeutic plaster, or if reactive materials, such as pharmaceutic substances, are incorporated into the surface. These substances are applied topically and may contact the skin only at the site of application, for example, active substances such as those proposed in German Patent Application P 39 01 551.3 for the treatment of actinic keratosis which are incorporated into a plaster system.

In order to solve the above mentioned problems, it has been proposed to provide straight cuts or predetermined breaking lines in the carrier or covering layer, respectively, so that by flexing and/or pulling-off the carrier or cover layer portions of it can be removed from the article which is adhesively connected to said layer. However, perfect, complete and simple exposure of the surface of the article or a corresponding removal thereof, respectively, is not guaranteed, particularly, if a sensitive article is concerned, such as, for example, a therapeutic plaster, a plastic moulding, a very flexible carrier or cover layer of a thin aluminum foil, an aluminum laminate, a polymer foil, or the like. Particularly in case of small articles having a small surface to be protected, it is difficult to expose it completely. But even the selective separation of individual sections of the article and carrier or cover layer has not been solved satisfactorily.

In U.S. Pat. No. 3,230,649 the provision of arcuate cuts or predetermined breaking lines in the carrier foil is described, which, on flexing the material, lead to a gripping tab of the carrier material so that this section can be peeled off. However, this solution does not provide a satisfactory process for complete and undamaged separation of the partners connected with each other, since, in general, a remaining portion of the carrier layer is to be laboriously removed from the article by means of the fingernails or an auxiliary tool.

It is also known in the use of several articles or several connected parts of an article, respectively, to connect them by means of a kind of releasing tape so that on pulling a projecting portion of the tape the parts connected by this tape can be removed from the carrier layer in one operational step. However, prior to use or application of the individual portions they have to be released from the releasing tape.

In addition to the relatively expensive production, this known arrangement is limited to the simultaneous removal of several articles or several parts of an article, respectively, and to relatively small articles or parts thereof. It is also known to provide strips or threads of suitable material, such as plastic, textiles, or metal, between a carrier layer and the articles positioned thereon, whereby these strips or threads project at least at one end from the articles or parts thereof so that separation will be possible. However, this arrangement and the formation thereof involves considerable expense, not to mention the fact that it cannot be applied in all cases.

In European Patent Application No. 0284963 a pulling-off aid according to FIG. 1 is proposed. The pulling-off aid is intended for mechanically removable substrates (1.2) adhering to a planiform, flexible carrier material (1.1). It consists of non-linear cuts or predetermined breaking lines (1.4) in the carrier material (1.1) for each individual substrate (1.2). By applying pressure on the carrier material (1.1) in vertical direction to the substrate contact surface, a portion of the substrate predetermined by the lines of the predetermined breaking lines or cuts is bendable in the direction of the substrate or substrates. By this, at least a portion of the substrate (1.2) in its edge region adjacent to the cut line or predetermined breaking line (1.4) is released from the carrier material (1.1) and thus provides a gripping section (1.3) at the substrate (1.2) in order to completely remove the substrate (1.2) from the carrier material (1.1).

The proposed solution of the problem permits easy removal of such adhesive substrates, however, requires contacting the adhesive substrate area with the fingers so that contamination of the fingers with reactive materials in the substrate becomes possible.

It is the object of the present invention to provide an application aid avoiding the above mentioned disadvantages of the known solutions and permitting removal of articles connected in an adhesive but mechanically releasable manner to a carrier or cover layer in an easy and reliable, given way without the necessity or danger of contamination of the contact or protective area.

This object is achieved according to the present invention with an application aid according to claim 1. Suitable further embodiments of the present invention are described in the subclaims.

The use of the application aid according to the present invention permits that each time an exactly predetermined portion of the carrier or cover layer with an article adhering thereto is easily and reliably separated from the carrier or cover layer in both cases, i.e., where only one article but also where a plurality of articles is connected to the carrier or cover layer in an adhesive but mechanically removable manner, whereby, at the same time, a predetermined portion of the protected surface of the article is exposed, thereby neither arising the necessity nor the danger of manual contact, and thus permits easy and comfortable transfer of the article to its intended purpose by means of the portion of the carrier or covering layer gripped by the hand.

Figure 2:
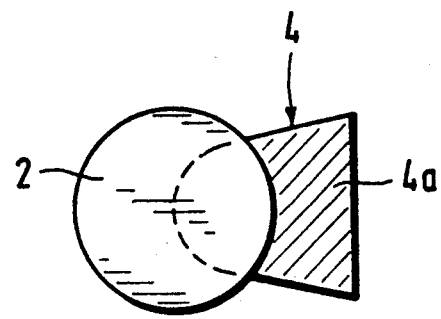
Figure 3:
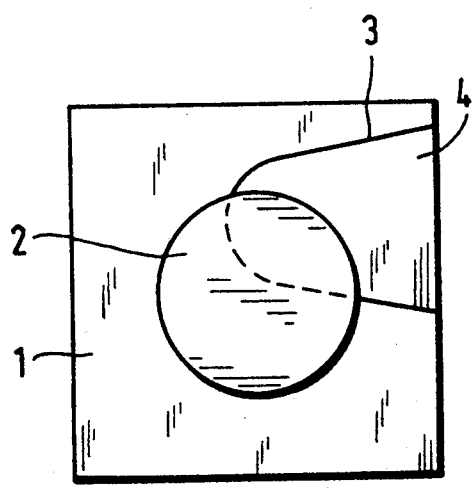
Figure 4:
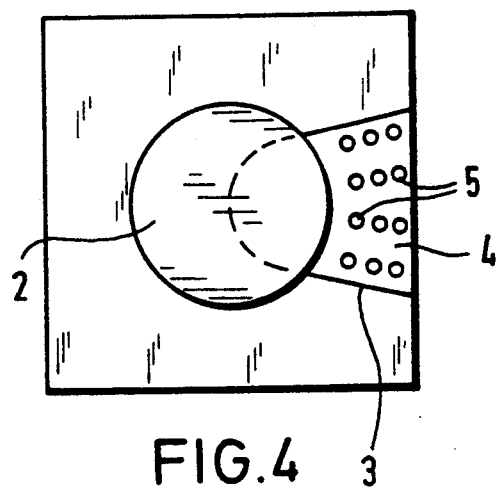
Figure 5:
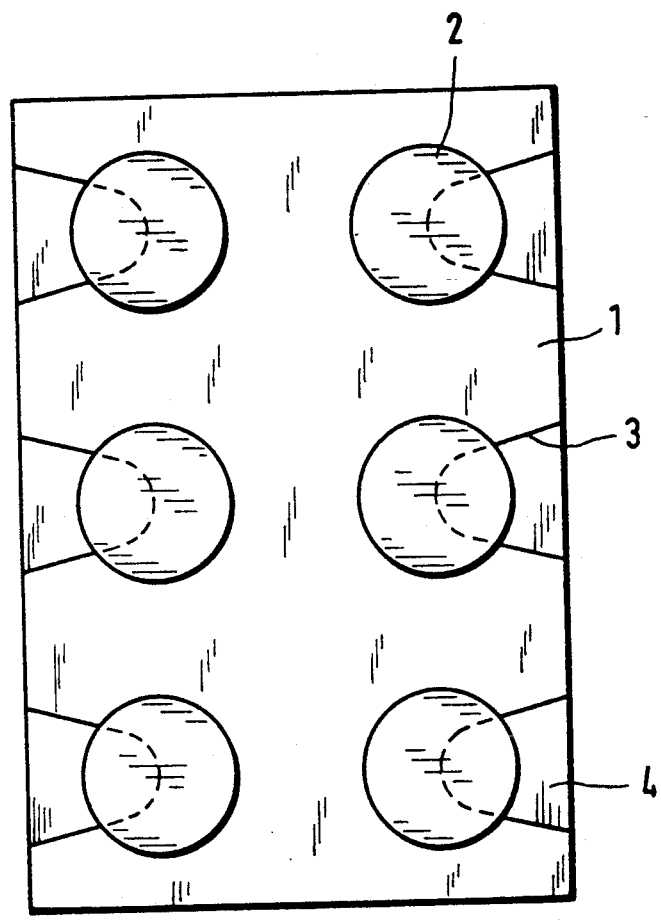

The invention is illustrated in the drawing as embodiment examples, and will be further explained with reference to the drawings, wherein FIG. 1 shows a square carrier or covering layer with a circular article positioned thereon, FIG. 2 shows a section of the carrier or cover layer which, together with the article, has been separated from the carrier or cover layer according to FIG. 1, FIG. 3 shows a modification of FIG. 1, FIG. 4 shows another modification of FIG. 1, FIG. 5 shows an embodiment example of an arrangement of a multiplicity of articles on a common carrier or cover layer, respectively.

According to FIGS. 1 and 2 the article 2 illustrated with circular cross-section is centrally positioned on the square carrier or cover layer 1, whereby the carrier or covering layer 1 and the article 2, which may be a label, a plaster, a therapeutic system, or the like, are to be connected with each other at their contact surface either contacting or opposing each other in an adhesive but mechanically releasable way.

The carrier or cover layer 1, starting from its right-hand edge, is provided—relative to an imaginary horizontal center line, symmetrically—with the substantially triangular cut or predetermined breaking line 3. This cut or predetermined breaking line 3 may, for example, be a notch or perforation extending over a portion of the thickness of the carrier or covering layer, whereby the perforation may exhibit a more or less large number of more or less closely arranged perforation holes having a more or less large cross-section. However, this cut or predetermined breaking line could also have the form of a more or less large number of more or less long indentations connected with one another by webs. As a matter of fact, in this connection, it is paid attention to the fact that the mechanical stability of the carrier or covering layer 1 is adequate to reliably prevent unintentional and too early separation—for example during packaging.

Depending on the sensitivity of the contact surface to be protected of the article 2, one may also form the cut or predetermined breaking line 3 in the region where it extends below the article 2 as notch not completely passing through the thickness of the carrier or cover layer 1, and in the regions extending outside of the article 2 as perforation or indents with webs lying in between. In any case, the formation is chosen in such a way that a reliable protection of the surface to be protected of the article 2 is guaranteed, however, that the portion 4 of the carrier or covering layer 1, which portion is determined by the cut or predetermined breaking line 3, can be separated easily and safely from the carrier or covering layer 1 in the defined way. In this connection, as a matter of fact, it has to be safeguarded that the area, at which portion 4 and article 2 adhere to each other, is chosen in such a way that both perfect removal of article 2 from the carrier or cover layer and the reliable adherence of article 2 to portion 4 is safeguarded when said portion is separated from the rest of the carrier or covering layer, respectively.

As is particularly obvious from FIG. 2, the hatched region 4a of the member 4 is sufficiently large so as to permit safe gripping for separation from the remaining portion of the carrier or covering layer 1.

As a matter of fact, any desired shape of the carrier or cover layer 1 can be realized instead of the square shape shown, the same applies to the article 2, i.e., instead of the circular shape, any other possible shape may be chosen, depending on the article of the respective case. Similarly the shape of member 4 can certainly be completely different from that as shown, just as is suitable or required. Finally, the central arrangement of the article 2 on the carrier or covering layer 1 is meant to be an example only, any other off-central or asymmetric arrangement of article 2 and arrangement and formation of member 4 could be chosen.

Such an asymmetrical arrangement of the part 4 in relation to the carrier or cover layer 1, and in particular to article 2, is shown in FIG. 3 in which the cut or predetermined breaking line 3 is displaced upward at the right edge so that the member 4 contacts the article 2 on an asymmetrically shaped area.

According to the circumstances, this asymmetric arrangement and formation can be suitable to facilitate the use or application of the articles 2, if the article 2, by means of the separated member 4 covering one portion of the area of the article 2 and projecting the article 2 by part 4a, is transferred to the site of application and applied thereto without touching the contact surface of the article. For this purpose, the exposed surface of the article is at first anchored to the site of application, then the separated part 4 of the carrier or cover layer 1 is removed, and finally the article is completely brought into contact with the site of application. In this connection the active-substance-containing or otherwise prepared surface of the article never has to be touched with the fingers or any other auxiliary instrument, such as forceps or the like.

In order to facilitate the separation or releasing process, respectively, the region 4a of the member 4 meant for gripping it with the hand is provided with elevations or knops 5, thus particularly ensuring safe gripping. Certainly, engravings or any other kind of elevations may also be provided for, instead of the knops.

An example of arranging and applying several articles 2 or even parts of an article on a common carrier or covering layer is shown in FIG. 5. As a matter of fact, in this case too, the symmetric shape of the carrier or cover layer 1, as well as the arrangement and form of the articles 2 and of the cut or predetermined breaking lines 3, and that of the tear-off portions 4 and gripping parts 4a formed by the cut or predetermined breaking lines are not compelling, what is more, any other suitable or desired form can be put into practice without having to accept any disadvantages.

It is understood that the specification and examples are illustrative but not limitative of the present invention and that other embodiments within the spirit and scope of the invention will suggest themselves to those skilled in the art.

We claim:

1. The combination of at least one article selected from the group consisting of a therapeutic system and therapeutic device, and a removable carrier or covering layer (1), said article being positioned on and adhering to said carrier or covering layer (1), said carrier or covering layer being substantially flat and flexible and having integral therewith an application aid for said article, said application aid defining a portion of said carrier or covering layer (4, 4a) and being detachable therefrom by severing guides, said article (2) being so positioned upon the carrier or covering layer (1) such that a portion of the article (2) is positioned over a part of the application aid and the severing guides.

2. The combination of at least one article (2) selected from the group consisting of a therapeutic system and therapeutic device, and a removable carrier or covering layer (1), said article being positioned on and adhering to said carrier or covering layer (1), said carrier or covering layer being substantially flat and flexible and having integral therewith an application aid, said aid defining a portion of said carrier or covering layer (4,4a) and being attached thereto and removable therefrom by severing guides, said article (2) being so positioned upon the carrier or covering layer (1) such that a portion of the article (2) is disposed over a part of the application aid and the severing guides, a portion of the aid not covered by the article being provided with a knop or engraving.

3. An application aid according to claim 2, wherein the removable portion (4) of the carrier or covering layer (1) is in contact with at least 10% of the article (2).

4. An application aid according to claim 2, wherein the removable portion (4) of the carrier or cover layer (1) is connected to the remaining part of the carrier or cover layer (1) via a few connecting webs.

5. An application aid according to claim 2, wherein the severing guides are partial cuts.

6. An application aid according to claim 2, wherein the severing guides are predetermined breaking lines.

7. The combination of at least one article (2) selected from the group consisting of a therapeutic system and therapeutic device, and a removable carrier or covering layer (1), said article being positioned on and adhering to said carrier or covering layer (1), said carrier or covering layer being substantially flat and flexible and having integral therewith an application aid, said aid defining a portion of said carrier or covering layer (4,4a) and being attached thereto and removable therefrom by severing guides, said article (2) being so positioned upon the carrier or covering layer (1) such that a portion of the article (2) is disposed over a part of the application aid and the severing guides, the position of the article upon the aid being asymmetrical.

* * * * *